(12) United States Patent
Goldsmith et al.

(10) Patent No.: US 7,156,597 B2
(45) Date of Patent: *Jan. 2, 2007

(54) CONTAMINATION DETECTION SYSTEM

(75) Inventors: Robert M. Goldsmith, Pasadena, CA (US); Catherine H. Goldsmith, Pasadena, CA (US); James G. Woodaman, Pasadena, CA (US)

(73) Assignee: SIRA Technologies, Inc., Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/366,684

(22) Filed: Feb. 11, 2003

(65) Prior Publication Data

US 2004/0018640 A1    Jan. 29, 2004

Related U.S. Application Data

(63) Continuation of application No. 10/164,289, filed on Jun. 5, 2002, now abandoned, which is a continuation-in-part of application No. 09/624,293, filed on Jul. 24, 2000, now Pat. No. 6,479,016, which is a continuation of application No. 09/352,309, filed on Jul. 12, 1999, now Pat. No. 6,190,610, which is a continuation of application No. 09/052,374, filed on Mar. 31, 1998, now abandoned, which is a continuation of application No. 08/758,205, filed on Nov. 26, 1996, now abandoned, and a continuation-in-part of application No. 08/584,984, filed on Jan. 11, 1996, now abandoned, which is a continuation of application No. 08/197,297, filed on Feb. 16, 1994, now abandoned, which is a continuation-in-part of application No. 08/064,521, filed on May 19, 1993, now Pat. No. 5,306,466, said application No. 09/624,293 is a continuation-in-part of application No. 09/287,950, filed on Apr. 7, 1999, now Pat. No. 6,270,724, which is a continuation-in-part of application No. 09/246,064, filed on Feb. 8, 1999, now abandoned, which is a continuation of application No. 09/052,361, filed on Mar. 31, 1998, now Pat. No. 5,869,341, which is a continuation of application No. 08/758,205, and a continuation-in-part of application No. 08/584,984.

(60) Provisional application No. 60/027,412, filed on Sep. 30, 1996.

(51) Int. Cl.
*F16B 13/06* (2006.01)

(52) U.S. Cl. .............................. 411/58; 422/61; 436/1; 426/232; 116/206

(58) Field of Classification Search ................ 436/1, 436/164, 166; 422/58, 61; 426/232; 116/206
See application file for complete search history.

(56) References Cited

U.S. PATENT DOCUMENTS

| | | |
|---|---|---|
| 2,485,566 A | 10/1949 | Clark |
| 3,067,015 A | 12/1962 | Lawdermilt |
| 4,285,697 A | 8/1981 | Neary |
| 4,746,616 A | 5/1988 | Honigs et al. |
| 4,929,818 A | 5/1990 | Bradbury et al. |
| 5,053,339 A | 10/1991 | Patel |
| 5,306,466 A * | 4/1994 | Goldsmith ............. 422/58 |

(Continued)

FOREIGN PATENT DOCUMENTS

EP      0117390      9/1984

(Continued)

*Primary Examiner*—Lyle A. Alexander
(74) *Attorney, Agent, or Firm*—Perkins Coie LLP

(57) ABSTRACT

A dual bar code for detecting contamination. When no contamination is present, a first bar code identifies the product. When contamination is present a second bar code identifies the presence of contaminants.

5 Claims, 8 Drawing Sheets

U.S. PATENT DOCUMENTS

| | | |
|---|---|---|
| 5,490,476 A | 2/1996 | Veitch et al. |
| 5,869,341 A * | 2/1999 | Woodaman .................... 436/1 |
| 6,190,610 B1 * | 2/2001 | Goldsmith et al. ........... 422/58 |
| 6,270,724 B1 * | 8/2001 | Woodaman .................. 422/58 |
| 6,479,016 B1 * | 11/2002 | Goldsmith et al. ........... 422/58 |

FOREIGN PATENT DOCUMENTS

| | | |
|---|---|---|
| JP | 60-169569 | 11/1985 |
| WO | 94/27144 | 11/1994 |

* cited by examiner

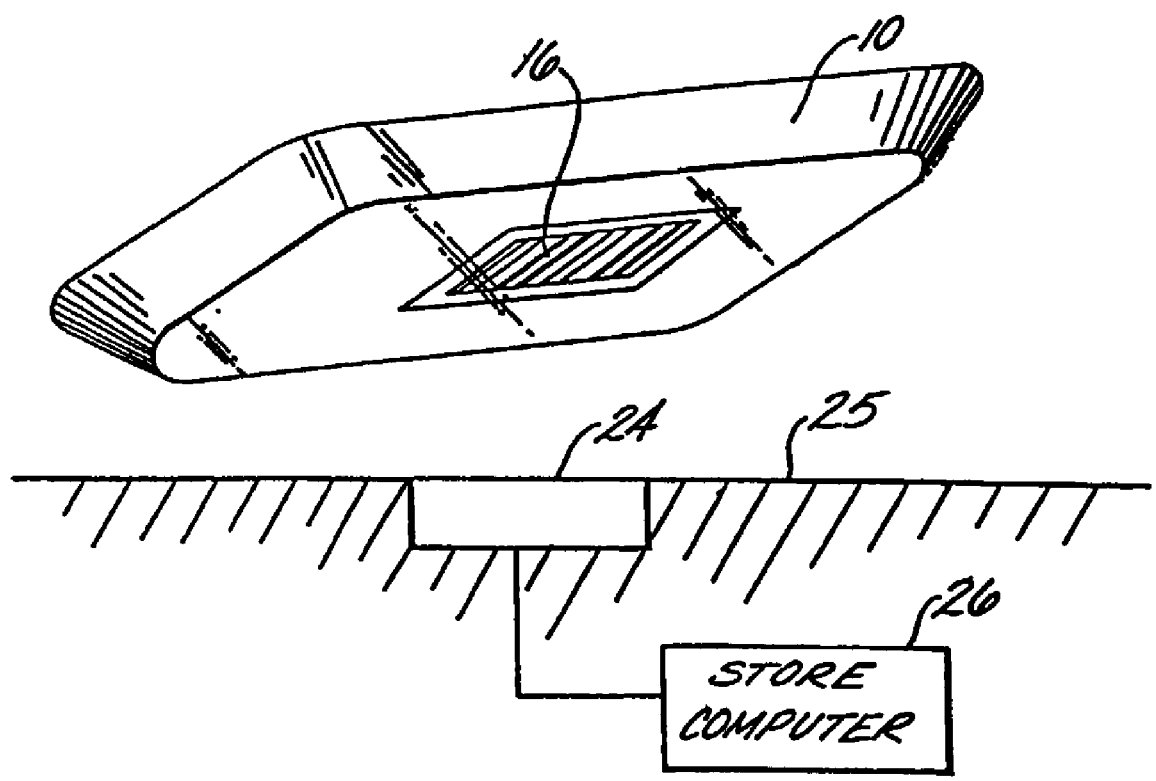

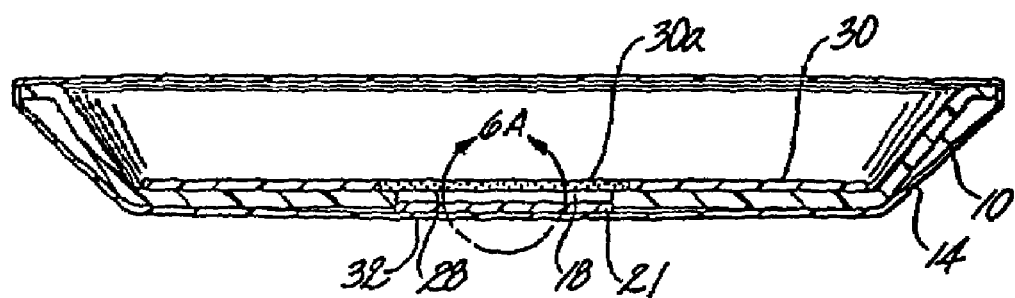
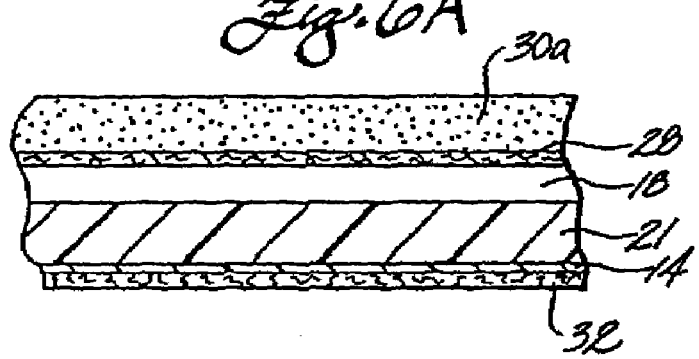
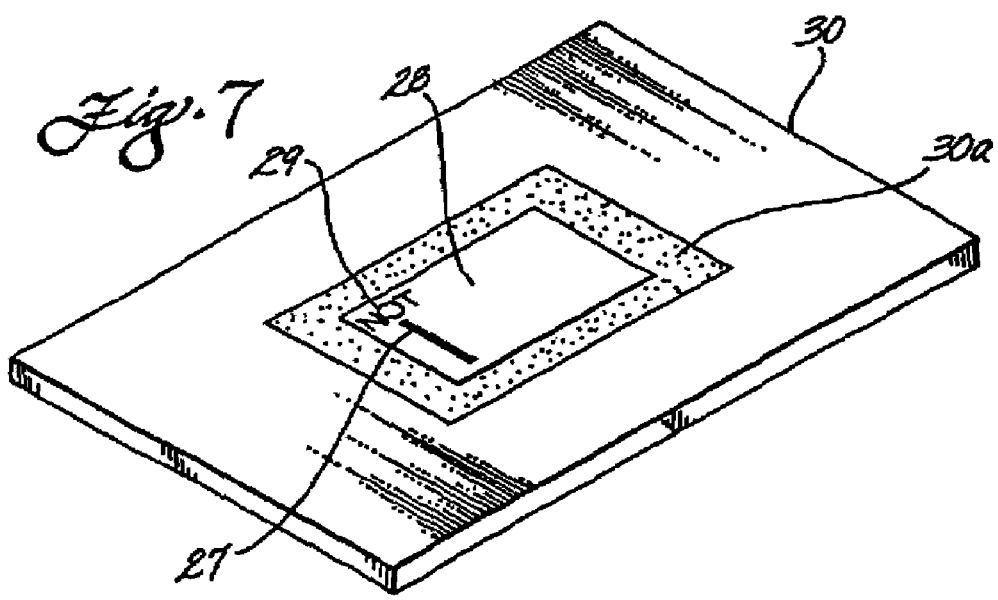

US 7,156,597 B2

CONTAMINATION DETECTION SYSTEM

CROSS-REFERENCE TO RELATED APPLICATIONS

This application is a continuation of 10/164,289, filed Jun. 5, 2002, now abandoned, which is a continuation-in-part application of U.S. application Ser. No. 09/624,293, filed Jul. 24, 2000, now U.S. Pat. No. 6,479,016 which is a continuation application of U.S. application Ser. No. 09/352,309, filed Jul. 12, 1999, now U.S. Pat. No. 6,190,610 issued Feb. 20, 2001, which is a continuation of U.S. application Ser. No. 09/052,374, filed Mar. 31, 1998, now abandoned which is a continuation of U.S. application Ser. No. 08/758,205, filed Nov. 26, 1996, now abandoned which claims the benefit of U.S. Provisional Application Ser. No. 60/027,412, filed Sep. 30, 1996 and which is a continuation-in-part of U.S. application Ser. No. 08/584,984, filed Jan. 11, 1996, now abandoned which is a continuation of U.S. application Ser. No. 08/197,297, filed Feb. 16, 1994, now abandoned which is a continuation-in-part of U.S. application Ser. No. 08/064,521, filed May 19, 1993, now U.S. Pat. No. 5,306,466 issued Apr. 26, 1994; U.S. application Ser. No. 09/624,293, filed Jul. 24, 2000 is also a continuation-in-part of U.S. application Ser. No. 09/287,950, filed Apr. 7, 1999, now U.S. Pat. No. 6,270,724 issued Aug. 7, 2001, which is a continuation-in-part of U.S. application Ser. No. 09/246,064, filed Feb. 8, 1999, now abandoned which is a continuation of U.S. application Ser. No. 09/052,361, filed Mar. 31, 1998, now U.S. Pat. No. 5,869,341 issued Feb. 9, 1999, which is a continuation of U.S. application Ser. No. 08/758,205, filed Nov. 26, 1996, now abandoned which claims the benefit of U.S. Provisional Application Ser. No. 60/027,412, filed Sep. 30, 1996 and which is a continuation-in-part of U.S. application Ser. No. 08/584,984, filed Jan. 11, 1996 now abandoned. The above mentioned applications are hereby incorporated by reference as if fully set forth herein.

FIELD OF THE INVENTION

The present invention relates to detection of the presence of microbial contaminants.

BACKGROUND OF THE INVENTION

Since the events of Sep. 11, 2001 and the subsequent anthrax incidences, there has been increasing concern bioterrorism and over contamination of the environment in which we live and work and contamination of items and packages that we come in contact with. Bioterrorists may employ a variety of organisms including *Bacillus anthracis* (Anthrax), *Clostridium botulinum* (Botulism), *Yersinia pestis* (Pneumonic plague), variola virus (Smallpox), *Francisella tularensis* (Tularemia) and *Brucella* species, namely *B. abortus* (cattle), *B. melitensis, B. ovis* (sheep, and goats), *B. suis* (pigs), and *B. canis* (dogs). Bioterrorists may also employ chemical weapons such as Distilled Mustard gas, Mustard gas, Nitrogen mustard gas, Lewisite, hydrogen cholride gas, and others.

Environmental contamination can come from a variety of sources and the type of contamination possible is often dependent on the type of contaminant involved.

Environmental contamination with microbes may involve the airborne distribution of pathogens, e.g. crop dusters, bombs, HVAC systems, mail envelopes, etc. There is a need for a reliable way to detect if an environment, particularly, a closed environment has been contaminated. Any solution to this problem should be relatively inexpensive and able to detect a number of agents capable of causing illness. It should also be simple to "read" so that a consumer, who does not have access to sophisticated testing equipment or specialized knowledge, can readily determine if the environment is free from contamination In addition, over the past several years there has been increasing concern over the safety of our food supply. Contamination of food can come from a variety of sources and the type of contamination possible is often dependent on the food involved.

Most animal derived food products, such as raw meat, are exposed to the possibility of contamination before, during or after processing. Such contamination comes from, for example, contact with fecal matter at the slaughter house, from handlers of the food products at any stage of the processing of the food products or from toxins, both naturally occurring and man-made, present in the environment where the food was grown or processed. In most cases, contamination is minor and, if the food is prepared properly, is not a serious threat to the consumer. However, while the contamination of food is generally low, i.e. few bacteria per gram of the food, if the food is not stored under satisfactory conditions or stored for long periods of time, contaminants, such as bacteria, grow to become a serious threat to the eventual consumer of the products. Even if the food products reach the market in an acceptable condition, subsequent treatment by the consumer may lead to the development of serious contamination of the food.

A number of incidents and factors have lead to the growing concern over the food supply. These include:

raw chicken and egg products have been found to be contaminated with Salmonella and inadequate cooking of such products has led to serious illness or death of persons who have consumed the contaminated products;

inadequately pasteurized milk products have been found to be contaminated with Listeria which has lead to serious illness or death of consumers of the products;

a highly toxic strain of *E. coli* has lead to the death of several people who consumed prepared beef products which had been inadequately cooked;

a number of toxins are known, such as ciguatoxins, which contaminate fish. These toxins are not inactivated or destroyed by cooking and so their presence in fish is a threat to any consumer of the product;

shell fish, such as oysters, concentrate any contaminants present in the water in which they grow and, since they are frequently eaten raw, pose a threat to the health of consumers; and fish is increasingly eaten raw which adds to the possibility of increased outbreak of illness from water borne contaminants.

The only means the consumer has of determining if the food they purchase is contaminated is by visual inspection and by smell. These are usually inadequate to detect contamination.

There is a need for a reliable way to detect if a food product purchased by a consumer is fit for consumption. Any solution to this problem should be relatively inexpensive and able to detect a number of agents capable of causing illness. It should also be simple to "read" so that a consumer, who does not have access to sophisticated testing equipment or specialized knowledge, can readily determine if the products they have purchased are free from contamination.

SUMMARY OF THE INVENTION

The present invention relates to a food contamination detector. The food contamination detector comprises an indicator bound to a substrate. The indicator is in communication with juices from food which are to be tested for the presence of a toxin.

A means for changing the color of the indicator when the toxin is present in the juices from the food is provided to indicate that the food is contaminated. In one embodiment of the invention the means for changing the color comprises a labeled antibody which dissociates from the substrate in the presence of a toxin. In another embodiment the means for changing color comprises a labeled antibody which binds to the substrate in the presence of a toxin. In another embodiment the change in color results in a change in a bar code.

The present invention further relates to a contamination detector. The contamination detector comprises an indicator with a means for changing the appearance of the indicator when contamination is present. The contamination detector may be attached to a surface or incorporated into a container or packaging for material. The term 'container' refers to a receptacle in which material is held or carried. In one embodiment the means for changing the appearance of the indicator comprises a labeled antibody which dissociates from the substrate in the presence of a contaminant. In another embodiment the means for changing appearance comprises a labeled antibody which binds to the substrate in the presence of a contaminant. In another embodiment the change in appearance results in a change in a bar code.

BRIEF DESCRIPTION OF THE DRAWINGS

These and other features and advantages of the present invention will be better understood by reference to the following detailed description when considered in conjunction with the accompanying drawings in which:

FIG. 5 is a schematic diagram of a bar code reader for use in the present invention;

FIG. 6 is a side sectional view of another embodiment of the bar code detector system in a package tray without food;

FIG. 6A is an enlarged view of part of FIG. 6;

FIG. 7 is a perspective view of the bottom of the liner of FIG. 6 with one component of the bar code attached;

DETAILED DESCRIPTION OF THE SPECIFIC EMBODIMENTS

The present invention uses an indicator which may be in the form of words, symbols, a bar code, or part of a bar code that identifies the product at point of purchase, sale, or distribution as a detector system for toxins and other contaminants that may be present in food products. As used herein toxin means chemicals or pathogenic organisms which may be transferred from food to the consumers of the food, or other agents which may be toxic or result in illness in the consumer of the contaminated food products.

In another embodiment an indicator, which may be in the form of words, symbols, a bar code, or part of a bar code, is used as a contamination detector. The contamination detector may be attached to a surface or incorporated into a container or packaging for material. The term 'container' refers to a receptacle in which material is held or carried. One of the functions of a contamination detector is for use in detecting the presence of a contaminant or contaminants in an environment, a container or any similar environment. The term contaminant refers to microbial contaminants, toxic contaminants, bacterial metabolites, microbial secretions, and other contaminants related to bioterrorism, including biological and chemical weapons, anthrax, small pox, botulism, and pneumonic plague, or which may be toxic or result in illness to those who come in contact with it.

The invention is described in the context of bar codes because this is currently the prevalent way to identify food products, including information about product type, quantity, price, unit price, and origin in a machine readable manner. The invention is applicable, however, to other product identifying systems, machine readable and/or readable to a human. When the term "visible" is used herein, it means visible or readable by a bar code reader or other scanning apparatus.

The same reference numbers are used throughout the drawings to identify similar parts or elements.

Figure 1:
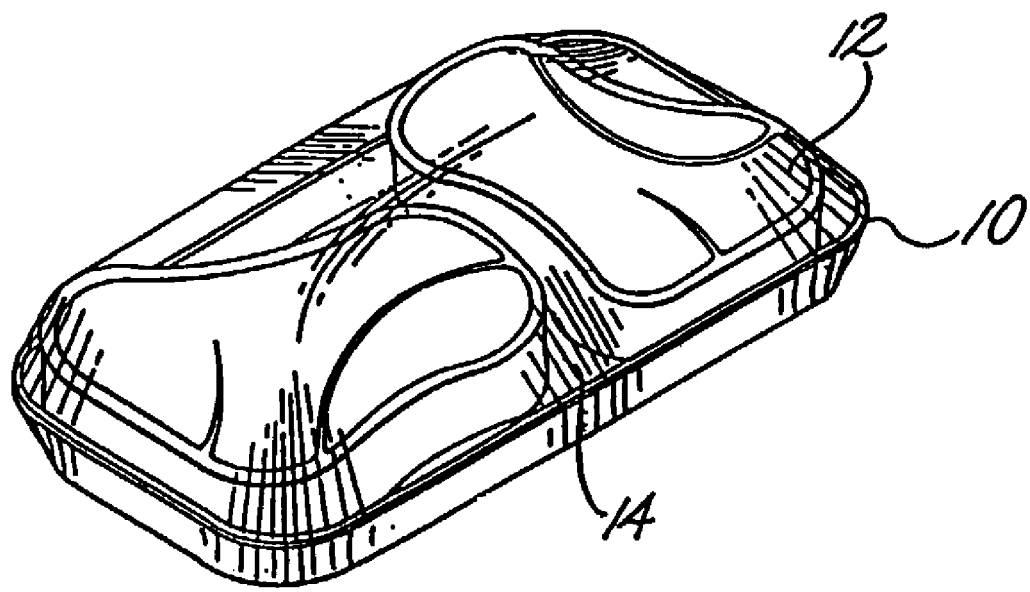
FIG. 1 is a top view of a packaged food product.
Figure 2:
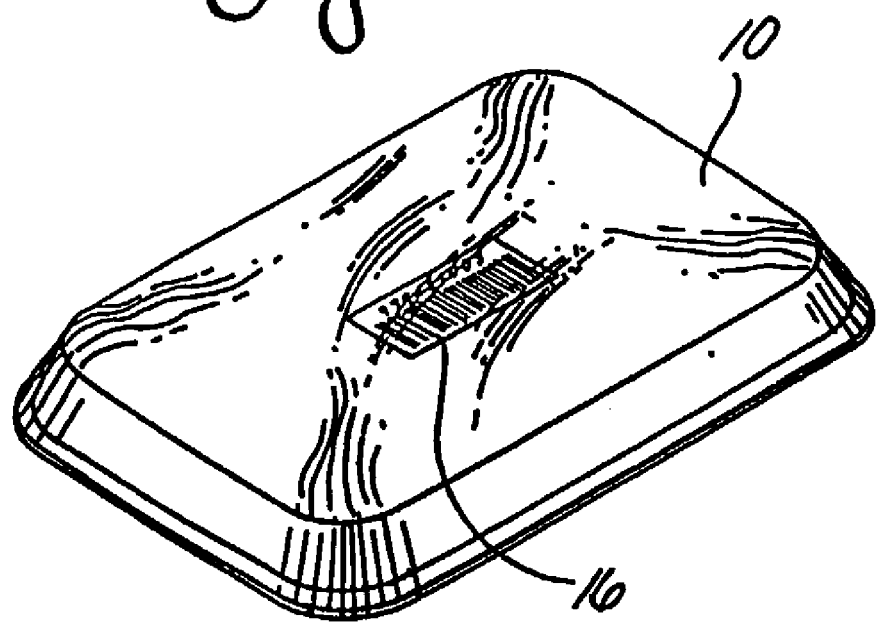
FIG. 2 is a bottom view of the packaged food product with a bar code detector system.
Figure 3:
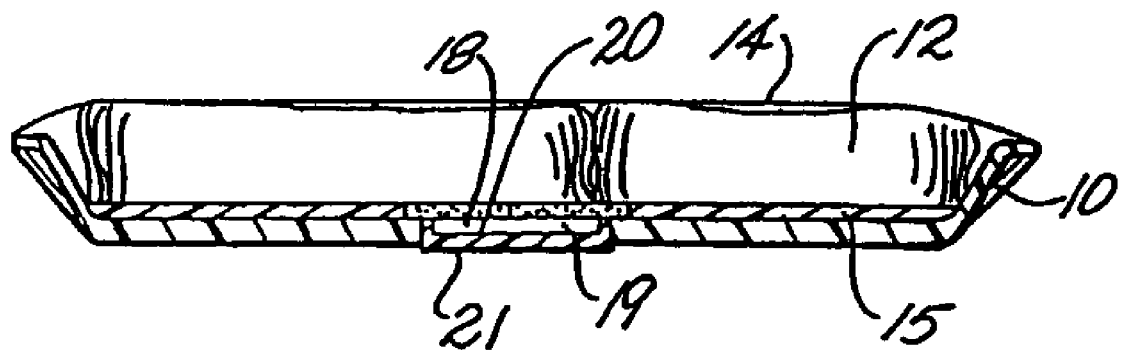
FIG. 3 is a side sectional view of the packaged food product showing the bar code detector system in the package.

Food products are often "mass produced" and sold at retail outlets, in prepackaged containers such as that illustrated in FIGS. 1–3. Typically, such packages include a styrofoam tray 10 which contains the food product 12; the tray and food are sealed in a transparent plastic wrap material 14 and a liner 15 lies between food product 12 and the inside bottom of tray 10. A bar code 16 is used on the products for scanning at the check-out register (FIG. 5), to reduce errors in totaling purchases and for stock control. The bar code comprises a series or pattern of bars which represent a number, identifying the product. In the practice of the present invention the product identifying system, e.g., the bar code, also serves the purpose of detecting toxins in the food products and/or detecting contamination in an environment or container.

In the embodiment of FIGS. 1–3, a bar code 16 is printed on a transparent membrane or substrate 20. One side of substrate 20 has a self-adhesive surface for attachment to the interior of tray 10 and the other side of substrate 20 has printed on it bar code 16. The bottom of styrofoam tray 10 has a rectangular hole 18.

Figure 4:
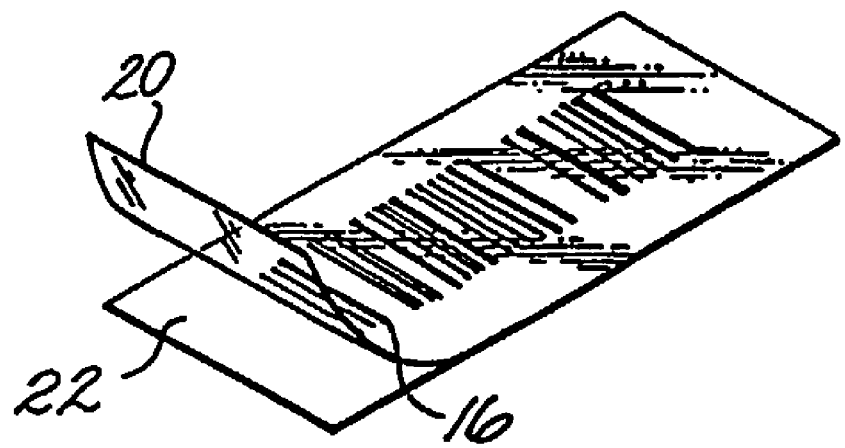
FIG. 4 is one embodiment of the bar code detector system of the present invention, prior to attachment to a food package.
Figure 8:
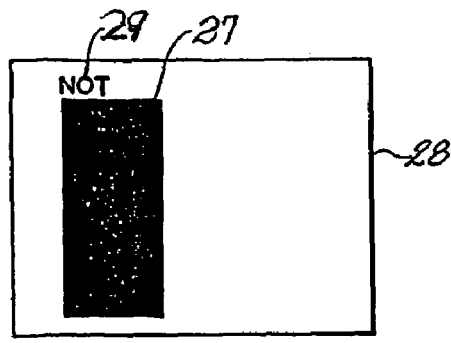
FIG. 8 is a front view of the component shown in FIG. 7.

Hole 18 is covered by a window 21 formed by a transparent sheet of material such as MYLAR® (a trademark of DuPont) using a suitable adhesive to seal the MYLAR to the styrofoam material around the edge of hole 18. Hole 18 and window 21 also serve as a collector 19 for liquids and juices from food product 12 so the latter can come into contact with bar code 16. Substrate 20 can be prepared with a peelable, disposable backing or protective release layer 22 (FIG. 4), which covers bar code 16 prior to its application to a package. At the site of packaging of food product 12, release layer 22 is peeled off and the adhesive side of substrate 20 is placed on the inside surface of window 21 so that bar code 16 faces the interior of the package and is exposed to the juices of food product 12. In conventional food packaging the entire liner is generally absorbent.

In the practice of the invention, only a small portion 15 of the liner slightly larger than substrate 20 is absorbent; the remainder of the liner is preferably impervious to food juices so that most of the food juices are channeled to substrate 20. The absorbent portion 15a of liner 15 is positioned in tray 10 in alignment with substrate 20 to maximize exposure of substrate 20 to the food juices. Instead of making a portion of liner 15 absorbent, a hole could be punched out of liner 15 and substrate 20 could be attached by adhesive to liner 15 around the edges of the hole. As an alternative to the described embodiment, substrate 20 could also serve as the window, in which case it would be attached to, cover, and seal hole 18 in tray 10.

This above described embodiment may be adapted for use with containers or for applying to a surface. For example, a container, packaging material or a surface such as a wall, may be substituted for the styrofoam tray 10. In an alternative embodiment, the substrate 20 may be attached to a surface, such as a wall, or on the interior of a container with the bar code portion exposed to the environment or the interior of the container.

The bar code is formed by labeled antibodies bound to antigens. The labeled antibodies function as an "ink" and are "printed" in a bar code pattern on the transparent substrate 20. First, the antigens are bound to the entire surface of substrate 20 or the portion of its surface on which the bar code is to be placed. Then, the bar code is applied to the antigen coated surface of substrate 20 by a bar code printer, using the labeled antibody as the ink.

Preferably, bar code 16 serves the normal product identifying function of a bar code, i.e., it represents price, price per unit, type of product, origin, and quantity or weight information. As illustrated in FIG. 5, food packages carrying the bar code detector system 16 are passed under a bar code scanner or reader 24 mounted on a counter 25 at the point of sale to read the product information in the usual way. The bar code scanner or reader need not be at the point of sale. For example, the bar code scanner or reader may be located at various points in the distribution chain. A store computer 26 processes this information to totalize the amount of purchase and to manage inventory.

The bar code for use in the invention is prepared by irreversibly binding an antigenic determinant of toxins or contaminants of interest to the transparent substrate. The antigenic determinant may be a small portion of the toxin, which is specific for that toxin, it may be the toxin itself, an analog of the toxin or other compound which is capable of "mimicking" the toxin, or pathogenic microorganisms, all of which are referred to herein as "toxins."

Substrates suitable for binding the toxin are well known in the art. If substrate 20 serves as window 21 it must be impervious to the food juices and other liquids. Suitable substrates include substrates such as those made from activated hydrophobic polyvinylidene, polyvinylidene difluoride, mixed esters of cellulose nitrate and cellulose acetate, hydrophobic polyvinylidene difluoride, hydrophilic polyvinylidene difluoride, laminated and unlaminated polytetrafluroethylene, microfiber glass, cellulose and polypropylene. Once toxins are bound to the substrate other binding sites, which remain on the substrate, are blocked by contacting them with an "inert" binding agent such as bovine serum albumin or other suitable blocking agent.

Once the toxin is bound to the substrate a labeled antibody, which exhibits a specificity for the toxin, also referred to herein as anti-toxin, is bound to the toxin. Antibodies suitable for use in the present invention include monoclonal and polyclonal antibodies. The preparation of such antibodies, specific for a desired toxin, are well known in the art. In some cases it may be necessary to conjugate the toxin to a protein to "mask" the toxicity of the antigen. Otherwise injection of the toxic antigen may result in the death of the animal in which the antibodies are to be prepared. Methods of conjugating compounds are well known in the art and one such method is described by Hokama et al., *Mycotoxins and Phycotoxins* 188, A Collection of Invited Papers at the Seventh International IUPAC Symposium of Mycotoxins and Phycotoxins, Tokyo, Japan 1988, pp. 303–310 (Elsevier Science Publishers, Amsterdam), which is incorporated herein by reference.

In one embodiment of the present invention the antibody is labeled with a colored latex bead. The preparation of antibodies labeled with colored latex beads is well known in the art. Such labeled antibodies may be prepared by diluting latex beads in a solution such as phosphate-buffered saline (8.1 mM $Na_2HPO_4$, 1.5 mM $KH_2PO_4$, 137 mM NaCl, 1.6 mM KCl ) and mixing the solution gently to suspend and distribute the latex beads in the solution. Preferably, about a 10% (wt/v) suspension of latex beads is diluted about 1:100, to give a suspension of about 0.1% (wt/v) latex beads. An antibody solution is added to the latex bead suspension. Preferably, about 0.3 to about 0.6 mg of antibodies are added for each mg of latex beads, however, this ratio will vary depending on the specificity and sensitivity of the antibody preparation and the type of support being used. The amount of antibody to be used for the preparation of labeled antibodies is derived experimentally, using different dilutions of the antibody preparation. After addition of the antibody, the solution is gently mixed and incubated at about 40° C. for about 16 to about 20 hours. At the completion of the incubation, the labeled antibodies are washed with phosphate-buffered saline, and the sensitivity and specificity of the labeled antibody preparation are tested.

The sensitivity and specificity of the labeled antibodies are tested by coating a substrate with a preselected amount of toxin. When contacted with the labeled antibody, the labeled antibody binds to the toxin, resulting in the development of the desired color on the substrate. The color which develops will not be washed off by rinsing in a solution such as phosphate-buffered saline. Binding of the antibody to the toxin results in the development of color for the bar code pattern forming a bar code detector system named by the owner of this invention the SIRA BART™ system. In effect, the labeled antibodies act as a type of "ink" so the bar code pattern can be visualized.

In use with raw meat products, the bar code detector system is exposed to juices from the meat. The juices collect in the collector and come in contact with the bar code detector system. If a toxin is present in the juices, the antibodies will release from the bar code pattern and bind to the toxins present in the juices, thus altering or destroying the bar code pattern. Such antibody type assays are in and of themselves well known in the art and are referred to as competitive assays. A consumer can detect the presence of the toxin in the food product by a visual inspection of the bar code. If the consumer does not notice the alteration of the bar code, it is detected by bar code reader 24 at the checkout counter (FIG. 5) because store computer is configured to emit an alarm to warn that an altered bar code has been detected. The contaminated products can then be replaced with non-contaminated products. Likewise, when the contamination detection system is exposed to a contaminant, the antibodies will release from the bar code pattern and bind to the toxins present within the environment or container, thus altering or destroying the bar code pattern. Thus, contamination of an environment, a container, or material in a container or package may be detected by visual inspection of the bar code or by a bar code scanner or reader.

A labeled antibody is one means of indicating the presence of a toxin or other contaminant in the juices of a food product or in a container. Those skilled in the art will be aware of other indicators such as chemical indicators, which are useful in the practice of the present invention. Instead of destroying the bar code, the bar code could be altered in some other way, e.g., by change of color, depending on the nature of the indicating system. In general, the alteration of the bar code is detectable by the bar code reader so contamination of products can be automatically determined by the electronics. Thus, the invention presents a format or vehicle to utilize existing toxin or contaminant indicating systems more effectively. The owner of this invention has named this format FOOD SENTINAL™, a contaminant interdiction system.

The bar code reader can also be used to indicate whether packaged products are in satisfactory condition at the time they left the supplier. If contaminated products are detected in the processing stream, the supplier can find out the source of contamination and implement remedial steps to ensure that the source of contamination is eliminated.

The same toxin could be used for all the bars of the bar code or one or more toxins could be used for different bars. In this way a number of contaminants or toxins can be detected by a single bar code. Contaminants may be grouped together based on their common association with food, bioterrorism, or a particular industry, or they may be tailored for a particular product or material. The bar code would not only indicate that the food or container was contaminated but would also indicate the type of contamination.

In another embodiment of the present invention shown in FIGS. 6–10, the contamination indicator is incorporated in a bar code having two components—one component inside the package and another component outside the package. A substrate 28 is attached to the bottom of a liner 30 having an absorbent portion 30*a* aligned with substrate 28. Portion 30*a* of liner 30 is an absorbent material that draws juices and other fluids away from the meat to the surface of substrate 28. Substrate 28 is preferably pervious to the juices of the food product, but it does not need to be transparent. The position of substrate 28 on liner 30 is precisely set. As illustrated in FIGS. 7 and 8, one component of the bar code comprises visible indicator elements 27 and 29 printed on the exposed surface of substrate 28. Indicator elements 27 and 29 may include a bar, a symbol, letters, or a combination thereof. In the illustrated embodiment indicator element 27 comprises a bar, given the trademark SIRA BART™ by the owner of this invention, and indicator element 29 comprises the word "NOT". Indicator elements 27 and 29 are printed on substrate 28 using labeled antibodies as "ink", as described above.

In this embodiment, the bottom of styrofoam tray 10 has a window 21 formed by a transparent sheet of material such as MYLAR® (a trademark of DuPont) using a suitable adhesive to seal the MYLAR to the styrofoam material. The liner and tray are designed so the liner can be precisely positioned in the bottom of the tray. For example, liner 30 could be dimensioned so that when it is placed in tray 10 it fills the bottom of the tray with substrate 28 in register with window 21. In this way, the close fit between liner 30 and tray 10 serves to insure that indicator elements 27 are precisely positioned with respect to the second component of the bar code, which is placed on the exterior of the bottom of tray 10 and wrap material 14. Alternatively, ridges (not shown) could be molded into the inside bottom surface of tray 10 to position liner 30 precisely and hold it in place.

As illustrated in FIG. 9, the second component of the bar code detector system comprises a word 35 and a plurality of bars 31 printed on an opaque substrate 32 with ordinary ink and cut out sections 33 and 34 die cut from substrate 32. Section 33 is smaller than bar indicator element 27. Section 34 is larger than word indicator element 29. Bars 31 perform the normal product identifying function of a bar code, i.e., they represent price, unit price, type of product, origin, and weight or quantity. Substrate 32 has the same dimensions as window 21 and is placed on the outside of wrap material 14 so substrate 32 coincides with window 21. As a result, the position of substrate 32 is precisely set relative to substrate 28 so that indicator elements 27 and 29 are aligned with cut outs 33 and 34, respectively, and are normally visible from outside the package. Indicator element 27 completely fills cut out section 33 and indicator element 29 fits totally within cut out section 34. In the illustrated embodiment, word 35 is "CONTAMINATED".

When substrates 28 and 32 are aligned, the first and second components fit together to form the bar code. As illustrated in FIG. 10A, the words "NOT CONTAMINATED" are visible from the exterior of the package and indicator element 27 and bars 31 can be read by a bar code reader when no contaminants are present in the food juices inside the package. When contaminants are present, the labeled antibodies from which indicator elements 27 and 29 are formed react with the toxin and are removed from the substrate 28. As illustrated in FIG. 10B, this leaves only word 35 and bars 31 visible. In the absence of element 27, the bar code reader senses that the bar code is "defective" and in the absence of element 29 humans can visually observe that the contents of the package is "CONTAMINATED".

Since it is desirable to detect different toxins in different food products, indicator element 27 could be placed in different locations on substrate 28 depending upon the toxin to be detected and cut out 33 could also be placed in different locations on substrate 32 depending upon the toxin to be detected so it is aligned with the locations on substrate 28.

Again, this above described embodiment may be adapted for use with containers or for applying to a surface. For example, a container, packaging material or a surface such as a wall, may be substituted for the styrofoam tray 10.

The described two component bar code detector system can be used to great advantage with the conventional bar code applicator machines used to mark food products in super-markets. Such machines have a conveyor on which wrapped food packages are transported past a weighing station and a bar code label application station into a temporary storage bin. At the label application station a label carrier roll is fed past a printer where the product information is printed on the bar code labels (substrate 32) and under a blade where the bar code labels are released from the carrier and picked up by one or more robot arms for delivery to the packages. A worker punches a product identification code into a key pad. A controller calculates from the product identification code and from the weight the product information to be printed on the label such as price, weight, unit price, and historical data, i.e., origin, and controls the printer to print the bar code pattern and alphanumeric characters on the labels. The controller coordinates, i.e., times, the operation so the labels are applied to the proper packages.

A preferred method will now be described for using the two component bar code with a modification of the conventional bar code applicator machines used to mark food products such as meat, poultry, or fish, in supermarkets. In a central processing plant, indicator elements 27 and 29 are printed on substrates 28 with a labeled antibody or other contaminant detector as ink; then substrates 28 are mounted on liners 30 in a precise relative position and packed in shipping cartons. Liners are so prepared in separate cartons for each of a number of different toxins or contaminants and tray sizes. The cartons are shipped-to the supermarkets or packaging facility where the food products are packaged in trays, wrapped, and bar code labeled with the bar code applicator machine. The packaging operation takes place in the following order:

1. For each different toxin or contaminant, one of the corresponding liners is placed in a tray sized for the particular liner.

2. The food product is placed in the tray.

3. The food product and tray are covered with the wrap material.

4. The package is placed in a bar code applicator machine and the product identification code is entered through the keyboard.

5. The package is weighed in the machine and transported by the conveyor to the label application station.

Figure 9:
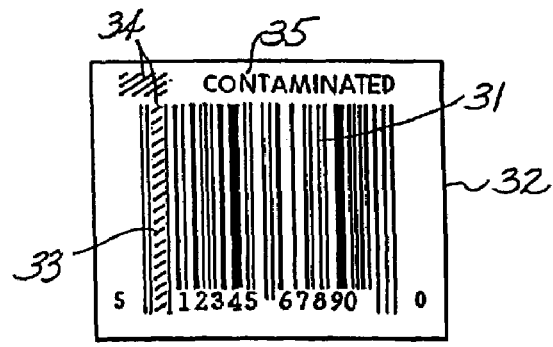
FIG. 9 is a front view of another component of the bar code detector system of FIG. 6.
Figure 10A:
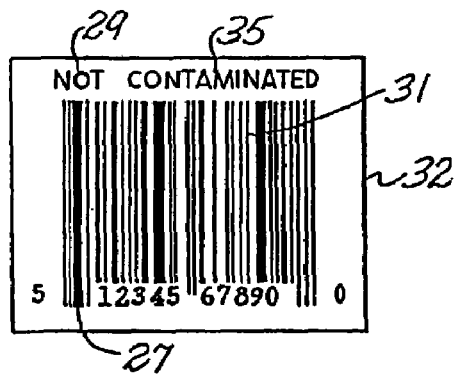
FIG. 10A is a front view of the components of FIGS. 8 and 9 as they appear from the outside of the food package in the absence of contamination.
Figure 10B:
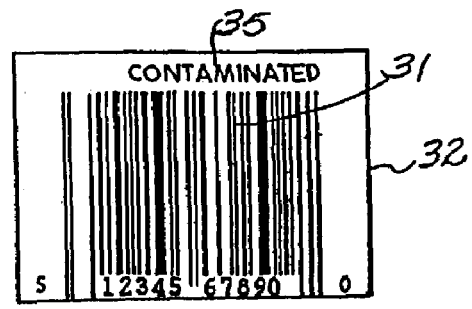
FIG. 10B is a front view of the components of FIGS. 8 and 9 as they appear from the outside of the food package in the presence of contamination.

6. The bar code applicator machine is modified to incorporate a label cutting die or die set in the path of the carrier between the roll and the printer. The die is adjustable in position and its position is set by the controller depending upon the particular product identification code. Each time a bar code label passes the die, the die is actuated by the controller to form the die cut sections (33 and 34 in FIG. 9).

7. The printer is operated by the controller to print words 30 and bars 31 on the bar code labels with ordinary ink.

8. The bar code labels are applied by the machine to a precise location on the outside of the packages in alignment with substrates 28 (FIG. 6).

In summary, the first component of the bar code, which requires tight manufacturing controls, is produced at a central processing plant. At the supermarket, workers without any special skill can reliably incorporate the first component into food product packages and add the second component of the bar code in the usual way, i.e. with a bar code applicator machine, or manually. The only special training for the workers at the supermarket is the proper selection and placement of the liner (30 in FIG. 6). If a worker makes a mistake in selection or placement of a liner, bar 27 is not aligned with cutout 34 and the bar code reader senses the mistake. This provides a check to ensure that the correct toxin detecting bar has been used with the correct food product.

Substrate 32 is preferably opaque and white, or at least light in color to create a strong contrast with the bar codes, which are preferably printed in a dark color. For this reason cutouts 33 and 34 are required so substrate 32 does not hide visual elements 27 and 29 of substrate 28. If sufficient contrast is otherwise available, substrate 32 can be transparent and the cutouts can be eliminated.

Instead of placing indicator element 27 and cutout 33 in different locations depending upon the contaminant to be detected, the location could remain fixed regardless of the type of contaminant and a visible symbol could be printed on substrate 32 near indicator element 27. For example, the letter "S" could be used for Salmonella, "E" could be used for *E. coli*, and "L" could be used for Listeria. This avoids having to incorporate an adjustable label cutting die in the bar code applicator machine.

In the embodiment of FIG., 11, the contamination indicator is also incorporated in a bar code detector system having two components—one component inside the package and another component outside the package. One component comprises a transparent bag 37 constructed from a bottom panel 36 and a top panel 38. Bag 37 is placed over hole 18 and the bottom panel 36 is secured to tray 10 by adhesive to seal hole 18 and form a window. Bottom panel 36 is fabricated from a substrate that is impervious to the food juices. A first antibody against the toxin of interest is bound to an area of the interior surface of bottom panel 36 identical in size and shape to or larger than hole 18. Top panel 38 is fabricated from a semipermeable membrane. The top and bottom panels are sealed together at their edges by use of an adhesive or other suitable method such as heat, to form a sealed bag, i.e., bag 37. Prior to sealing the bag a solution including a labeled second antibody against the toxin of interest is introduced into the bag. Although the first and second antibodies could be the same, they are preferably different. Thus, the second antibody preferably recognizes different antigenic determinants on the toxin than the first antibody. The second antibody is labeled with an indicator such as a colored latex bead so that the resultant labeled antibody is of a large size. The labeled antibody, present in the solution, is at a dilute concentration so that light will readily pass through the solution and so that little or no color is discernable.

The semipermeable membrane has a pore size which is large enough to allow the toxin of interest to enter the bag, but which is small enough to prevent the labeled antibody from leaving the bag. Such membranes are well known in the art and are commercially available in a variety of pore sizes. The pore size of the semipermeable panel is selected so that the toxin of interest will pass through the semipermeable panel to the interior of the bag.

When a toxin is present in the juices of a meat product packed in the tray, the toxin passes into the bag through semipermeable panel 38 and binds to antibodies bound to panel 36. The toxin also binds to the labeled second antibody present in the solution in the bag. As a result, panel 36 becomes colored by the sandwich assay of the first antibody, the toxin, and the labeled second antibody, thereby indicating the presence of a toxin in the juices.

The second component comprises bar code 16 printed on substrate 24, which is a transparent material such as MYLAR™. Substrate 20 is placed over hole 18 on the exterior of the met tray, and preferably outside wrap material 14. When a toxin is not present in the juices panel 36 remains clear and the bar code can be easily read against the clear background. When a toxin is present in the juices, the toxin binds to panel 36 and to the labeled antibody such that the substrate background becomes densely colored. In a preferred embodiment the color of the beads used is black and the uncolored background is white or clear. The dense color of the first component prevents the bar code of the second component from being distinguished from the background by the bar code reader. This effectively obliterates or changes the bar code and indicates that the food contained in the package is contaminated.

Again, this above described embodiment may be adapted for use with containers or for applying to a surface. For example, a container, packaging material or a surface such as a wall, may be substituted for the styrofoam tray 10.

Figure 11:
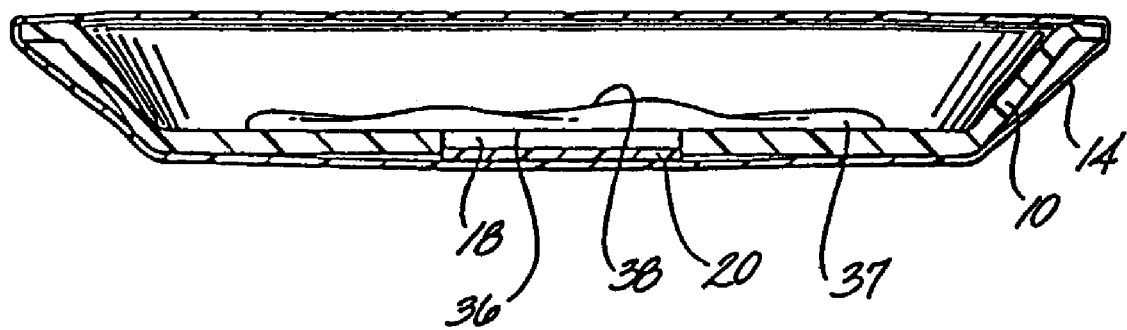
FIG. 11 is a side sectional view of another embodiment of a bar code detector system in a package tray without food.
Figure 12:
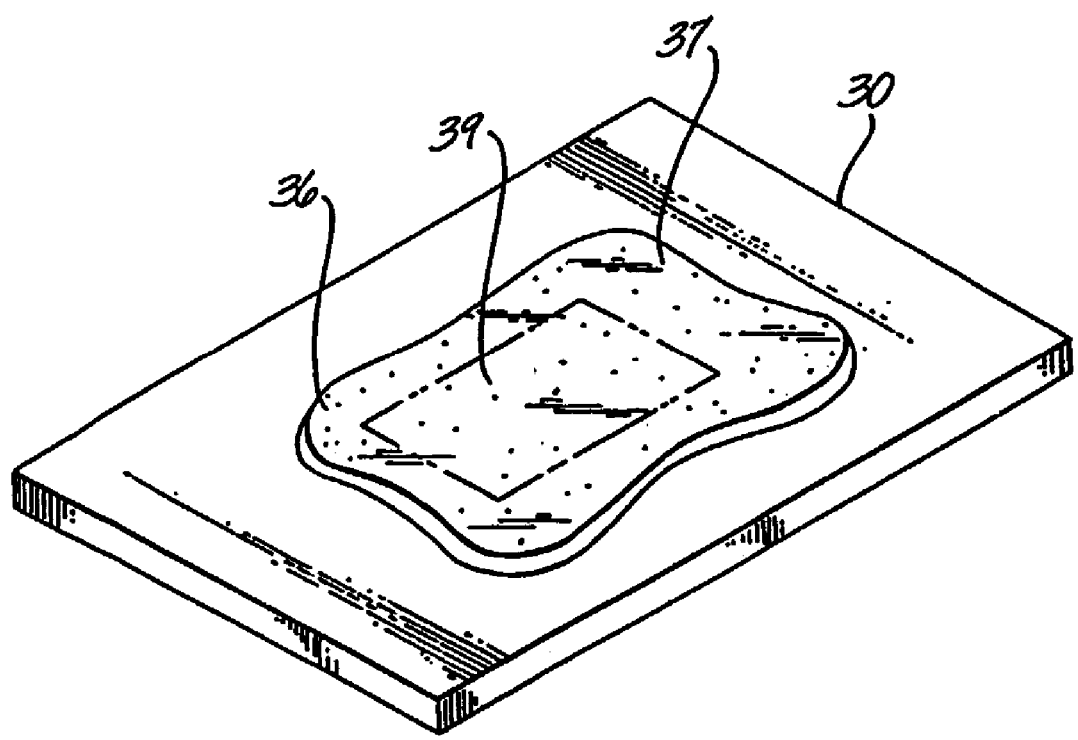
FIG. 12 is a perspective view of a liner for use in a variation of the bar code detector system of FIG. 11.

A variation of the two component bar code detector system of FIG. 11 is partially illustrated in FIG. 12. Panel 36 is secured to the underside of liner 30 using an adhesive or other suitable means of attachment. The portion 30 (not shown) of liner 30 covered by panel 36 is an absorbent material that draws juices and other fluids away from the meat to the surface of semipermeable panel 38 and serves to align bag 37 with hole 18, in the manner described in connection with FIG. 6. The remainder of liner 30 is impervious to food juices. The juices pass through the semipermeable panel 38 and into the interior of bag 37. On the interior of surface of panel 36 antibodies are attached as described above. The antibodies are attached to a rectangular area 39 on the inside surface of panel 36 such that when the liner is placed in the food tray rectangular area 39 aligns with hole 18. Substrate 20 is attached to the outer surface of tray 10 after tray 10 has been covered with wrap material 14. A bar code is printed on substrate 20 by the bar code applicator machine. The presence of toxins are then detected as described above.

Figure 13:
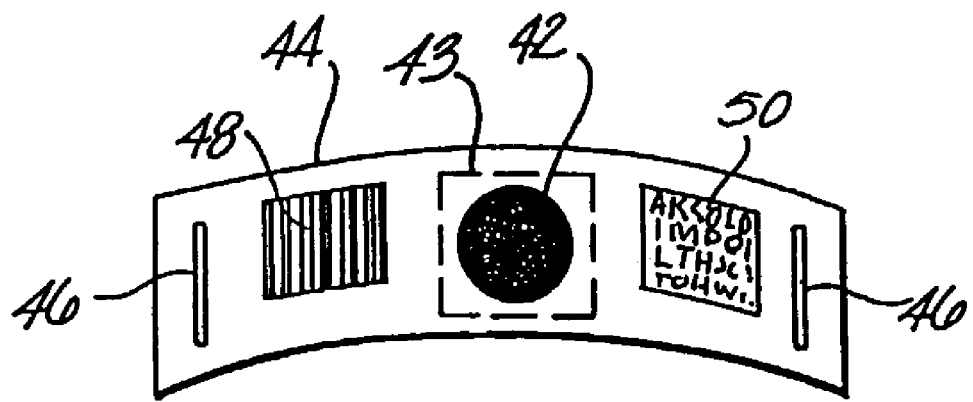
FIG. 13 is a perspective view of a carcass indicator strip incorporating principle of the invention prior to reaction with toxins.
Figure 14:
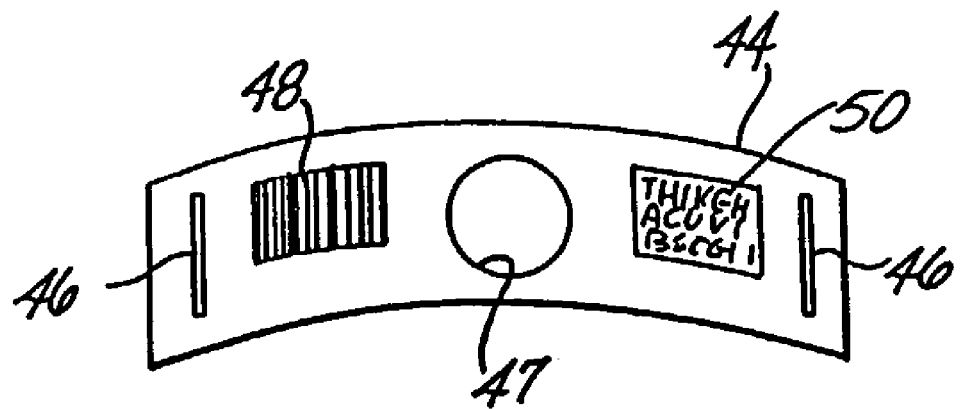
FIG. 14 is a perspective view of the carcass indicator strip of FIG. 13 after reaction with toxins.

In another embodiment of the invention shown in FIGS. 13 and 14, a symbol such as a colored dot 42 is printed on a square porous substrate 43. Substrate 43 is designed to be attached to the surface of a beef carcass or other bulk food product to determine if the carcass is contaminated. The "ink" used to print the dot is labeled antibodies attached to toxin as described above. An opaque holder strip 44 covers and secures substrate 43 in place. Substrate 43 and hold strip 44 comprise flexible material, which fits the contour of the carcass and keeps substrate 43 in contact with the surface of the carcass. A circular hole 47 is cut in the holder strip in alignment with substrate 43, so that when the substrate and holder strip are attached to the carcass, colored dot 42 is visible. If toxins are present in the meat of the carcass, the antibody becomes unbound from the surface of substrate 43 and the dot disappears to indicate the presence of toxins in the carcass. Holder strip 44 is attached to the carcass by use of stainless steel staples 46. The holder strip may also be used to display other identifying information, such as a bar code 48 and printed matter 50. Bar code 48 and printed matter 50 could be printed with ordinary ink.

Figure 15:
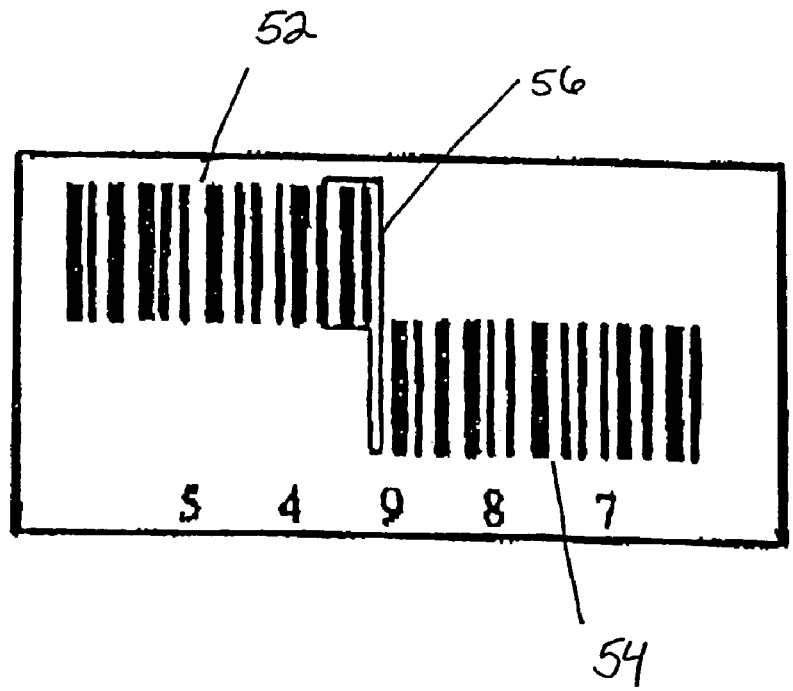
FIG. 15 shows a two bar code detector system which has not detected food contamination.
Figure 16:
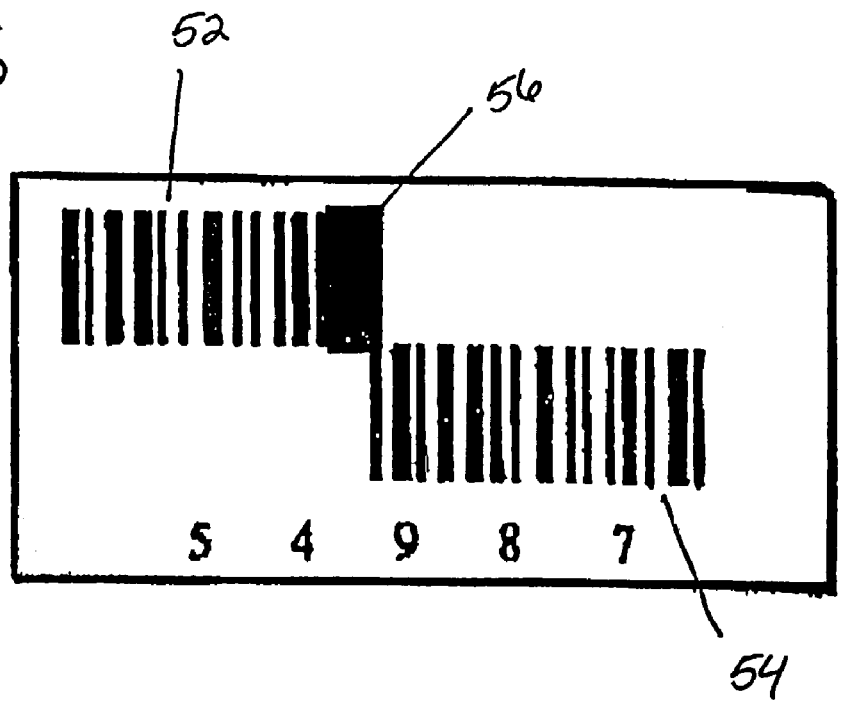
FIG. 16 shows a two bar code detector system which has detected food contamination.

A further embodiment of the bar code detector system is depicted in FIGS. 15 and 16. FIGS. 15 and 16 illustrate a two bar code food contamination detector system given the trademark GILBAR™ by the owner of their invention. The GILBAR™ has a product identification bar code 52 and a contamination detecting bar code 54. Additionally the GILBAR™ has a contamination indicator area 56 which is outlined in FIG. 15 by black lines for ease in visualizing the invention; however, in practice, these lines are not present so there is no interference with a bar code scanner or reader's ability to recognize product identification bar code 52.

The GILBAR™ food contamination system alerts consumers and anyone involved at any stage in food distribution using bar code scanners or readers that a food item is contaminated as follows. This embodiment of the invention is likewise adaptable as a contamination detection system for containers that would allow a consumer, end-receiver or anyone involved at any stage in the distribution of the container to determine whether the container has been contaminated.

In FIG. 15 the GILBAR™ has not detected contamination. Product identification bar code 52 will be read by a bar code scanner of reader, whereas contamination detecting bar code 54 will not be read. As shown in FIG. 16, when the food item or container becomes contaminated, the contamination indicator area 56 will change color obliterating a portion of product identification bar code 52 and adding an additional bar to contamination detecting bar code 54. Consequently, when the food product or container is contaminated, product identification bar code 52 cannot be read by a scanner or reader, whereas contamination detecting bar code 56 will be read. Typically, data from bar code scanners is transmitted to a computer or some centralized data collection for accounting, regulatory compliance of other reasons. The ability to detect contaminated food products or containers by bar code scanning creates an electronic record of whether or not a food product or container was contaminated from the point of sale to the consumer or end-user back through the chain of distribution.

This system is particularly advantageous to alert consumers in a grocery store or supermarket: environment which typically uses fixed bar code scanners. Fixed bar code scanners which are often mounted in checkout counters generate a plurality of scanning lines in three dimensional space which is often referred to as the "sweet spot." Supermarket or grocery store checkout clerks typically orient the bar code so it faces the scanner and sweep the product over the scanner window. This method allows for rapid identification and pricing of products occasionally, when a bar code is not read the checkout clerk will type in the product identification code to allow identification and pricing of the product with the unreadable bar code with the GILBAR™, when the product identification code is readable the contamination detecting bar code is not readable, and vice versa. Thus, when the food item is contaminated the product identification bar code will not be read, the contamination detecting bar code will be read, the consumer will be warned. This warning could be an alarm or a warning that would appear on the checkout register display such as the words "adulterated", "contaminated", "spoiled", or other such terms.

This system is also advantageous to alert end-users or receivers of a container that the container is contaminated. The end-user or receiver of a container may visually be alerted of contamination or a scanner or reader may be used.

The product identification numbers may or may not be present. If they are present, the indicator area 56 of the GILBAR™ would obliterate part of the product; identification code rendering it incomplete to avoid the accidental checkout of contaminated product. Additionally, the GILBAR™ indicator area 56 could include a number which appears upon contamination to complete a numeric code corresponding to the data coded by contamination detecting bar code 54. With these additional elements, a checkout clerk could not inadvertently price contaminated product when bar code 54 is not recognized or read by the scanner or an end-user or receiver would be alerted not to open or use the material in a container.

The GILBAR™ is based upon the same principles previously described herein. Instead of bars appearing in indicator area 56 the bars could disappear when a toxin is present. In this case one or more bars would disappear from product identification bar code 52 rendering the bar code unreadable while an additional bar or other element would disappear from the contamination bar code area of indicator area 56 rendering the contamination bar code 54 readable. Similarly, one or more digits of the optional pricing code could disappear from the bar code label rendering the code for product identification useless. Meanwhile, an extra number or a colored background in the indicator area where the contamination numeric code is located could disappear exposing the numeric contamination code.

The GILBAR™ can be used inside the package as described herein with reference to FIGS. 1–5 with bars appearing or disappearing using antibodies labeled with colored latex beads for the bar code "ink" on a substrate 20. Alternatively, the GILBAR™ can be employed with a portion of the GILBAR™ inside the package and a portion outside the package as described herein with reference to FIGS. 6–10. In the inside/outside arrangement the bar code elements found in the indicator area 56 are located on substrate 28 with the remaining elements of bar codes 52 and 54 aligned on the outside of the package with the interior indicator bars. In another embodiment, the indicator area 56 and the contamination detecting bar code 54 are located inside the package while the product identification bar code 52 is located on the outside of the package. This arrangement enhances the ability to track the source of contamination and still allows the processor, distributor and retailer to change the product identification bar code.

The present invention is not to be limited to the specific embodiments shown which are merely illustrative. Various and numerous other embodiments may be devised by one skilled in the art without departing from the spirit and scope of this invention. For example, with respect to the embodiments of the present invention illustrated in FIGS. 6–12, while the invention is described for use with antibodies against a single toxin, mixtures of antibodies, against a number of different toxins could be used. With the use of different antibodies, multiple, different toxins which could be present in the meat sample can be detected. Also, while the invention is described primarily in relation to obliterating a bar code, the antibody bound to the substrate could also be in the form of a symbol or wording which appears, or disappears depending on the type of antibody-toxin "assay" used. Such a symbol or wording could be read without the aid of a bar code reader. Also while some embodiments are described in conjunction with a liner, these bar codes could also be used in the absence of a liner. Similarly, embodiments described without a liner could be used in conjunction with a liner. The scope of the invention is defined in the following claims.

We claim:

1. A dual bar code system for detecting contamination comprising:

a first bar code symbol coded to identify a product;

a second bar code symbol separate and distinct from the first bar code symbol coded to identify contamination of the product, wherein the second bar code symbol comprises an indicator area for changing the appearance of the second bar code;

wherein when contamination is present, the appearance of the first bar code changes precluding product identification, and the appearance of the second bar code changes to identify contamination.

2. The dual bar code system of claim 1 wherein said system includes an antibody.

3. The dual bar code system of claim 1 wherein said system comprises a monoclonal antibody.

4. The dual bar code system of claim 2 wherein said antibody is associated with a label.

5. The dual bar code system of claim 4 wherein said label further comprises an immunobead.

* * * * *